US007472023B2

(12) United States Patent
Leu et al.

(10) Patent No.: US 7,472,023 B2
(45) Date of Patent: Dec. 30, 2008

(54) GAS ANALYSIS SYSTEM AND METHOD

(75) Inventors: Gen-Hou Leu, Taipei (TW); Shin-Fu Chiou, Keelung (TW); Shao-I Yen, Hsinchu (TW); Kuang-Sheng Wang, Kaosiung (TW); Hui Ya Shih, Changhua (TW)

(73) Assignee: Industrial Technology Research Institute, Hsinchu (TW)

( * ) Notice: Subject to any disclaimer, the term of this patent is extended or adjusted under 35 U.S.C. 154(b) by 230 days.

(21) Appl. No.: 10/653,746

(22) Filed: Aug. 29, 2003

(65) Prior Publication Data

US 2004/0124357 A1     Jul. 1, 2004

(30) Foreign Application Priority Data

Dec. 31, 2002   (TW) .............................. 91138113 A

(51) Int. Cl.
*G06F 19/00* (2006.01)
(52) U.S. Cl. .......................................... 702/27; 73/1.02
(58) Field of Classification Search ................... 702/27, 702/23, 24, 28, 30, 32, 189, 85, 88; 73/23.2, 73/23.34, 30.01, 1.02, 1.03
See application file for complete search history.

(56) References Cited

U.S. PATENT DOCUMENTS 4,038,055 A     7/1977  Varano et al.
5,227,631 A *   7/1993  Hunter et al. ............... 250/352
5,982,486 A *  11/1999  Wang .......................... 356/451
6,134,004 A *  10/2000  Reagen et al. ............... 356/451
6,714,304 B2 *  3/2004  Ota ............................. 356/451
6,748,334 B1 *  6/2004  Perez et al. .................. 702/24
6,862,534 B2 *  3/2005  Sterling et al. ............... 702/23
6,862,535 B2 *  3/2005  Binder ......................... 702/24
6,885,965 B2 *  4/2005  Butler et al. ................ 702/130
6,952,945 B2 * 10/2005  O'Brien ..................... 73/23.35
6,975,944 B1 * 12/2005  Zenhausern ................. 702/22
7,194,369 B2 *  3/2007  Lundstedt et al. ........... 702/104
2004/0133363 A1 * 7/2004  Vaidyanathan et al. ........ 702/30
2004/0197234 A1 * 10/2004 Endo et al. ............... 422/82.11

* cited by examiner

*Primary Examiner*—Edward Raymond
(74) *Attorney, Agent, or Firm*—Quintero Law Office

(57) ABSTRACT

A gas analysis system. The system includes a Fourier transform infrared (FTIR) spectrometer, a signal transformation module, an unknown chemical analysis module, a calibration model determination module, and a gas concentration calculation module. The signal transformation module receives electronic signals corresponding respectively to background and sample interferograms corresponding to a sample gas from the FTIR spectrometer for further calculation to obtain an absorption spectrum of the sample gas. The unknown chemical analysis module qualitatively analyzes the absorption spectrum of the sample gas to determine the chemical species in the sample gas. The calibration model determination module decides a calibration model. The gas concentration calculation module calculates the gas concentration of each chemical species according to the absorption spectrum, the calibration model and a standard spectrum of the chemical species.

18 Claims, 4 Drawing Sheets

GAS ANALYSIS SYSTEM AND METHOD

BACKGROUND OF THE INVENTION

1. Field of the Invention

The present invention relates to an analysis system and method for an unknown substance, and particularly to a gas analysis system and method that automatically detects the species and corresponding concentration of unknown substances using the absorption spectrum thereof.

2. Description of the Related Art

The monitor of species and concentration of gas and quality of air has become an important issue in the area of environmental security and hygiene. For example, if process piping is leaking, the species and concentration of the leaked gas will seriously affect the quality of process, and operators may be endangered. Conventional gas detection means uses a specified sensor to analyze specified gas. Since it cannot analyze all unknown substances (gas), it has limited application in industry.

Another conventional method uses a Fourier transform infrared (FTIR) spectrometer to analyze species of molecule. The FTIR spectrometer includes an IR source, an interferometer, an optics system and a detector, and obtains the interferogram of the molecule according to the interference theorem of light. The interferogram is a relational diagram of the intensity of IR source and time. Then, the interferogram can be transformed into a frequency-based absorption spectrum using Fourier transformation according to a reference (background) interferogram, and the chemical species and concentration of the molecule can be recognized using the spectral lines of the absorption spectrum and Bill's law.

When the dipole distance between molecules is changed and the energy provided by the IR source equals the transition energy between the molecules, the molecules may absorb the IR source and generate the IR absorption spectrum. The IR absorption spectrum is different from the molecules, and it is an effective tool to recognize and determine the chemical species and concentration of the molecules.

However, all of the gas analysis methods are operated manually, and make comparisons with sample spectra one by one. If the gas is complex, and if unknown substances appear in the gas, the analysis is time-consuming. Further, the obtained species and concentration are only checked for fulfillment of regulation, and there are no further applications thereto.

SUMMARY OF THE INVENTION

It is therefore an object of the present invention to provide a gas analysis system and method that automatically detects the species and concentration of unknown substances using the absorption spectrum of the unknown substance.

Another object of the present invention is to provide a gas analysis system and method that can be remotely monitored through a wireless network or Internet.

Another object of the present invention is to provide a gas analysis system and method that integrates with an alarm apparatus or fab monitor system, and sends an alarm signal if the concentration of any unknown substances exceeds a respective preset value.

To achieve the above object, the present invention provides a gas analysis system and method. The gas analysis system according to the embodiment of the present invention includes a Fourier transform infrared (FTIR) spectrometer, a signal transformation module, an unknown chemical analysis module, a calibration model determination module, a gas concentration calculation module and an alarm system control module.

The signal transformation module receives electronic signals corresponding respectively to a background interferogram and a sample interferogram corresponding to a sample gas from the FTIR spectrometer for further calculation to obtain an absorption spectrum of the sample gas. The unknown chemical analysis module qualitatively analyzes the absorption spectrum of the sample gas to determine the chemical species contained therein. The calibration model determination module builds and decides a calibration model used to calculate the concentration of each chemical species in the sample gas. The gas concentration calculation module calculates the gas concentration of each chemical species according to the absorption spectrum and the calibration model. The alarm system control module sends an alarm signal if the gas concentration of any chemical species exceeds its respective preset value.

The gas analysis system further includes a trend display module and a species information search module. The trend display module displays the trend of the gas concentration of each chemical species of the times in figures. The species information search module retrieves related information from a species information database according to the chemical species, and displays the related information of the chemical species in a display interface if the gas concentration of the chemical species exceeds its respective preset value and the alarm system control module sends the alarm signal.

The gas analysis system further includes a cooling system to automatically replenish coolant in the detector of FTIR spectrometer. If the signal transformation module cannot receive electronic signals from the FTIR spectrometer, the signal transformation module sends a signal to enable the cooling system to replenish coolant in the detector of FTIR spectrometer.

The gas analysis system further includes a remote monitor module to provide a client to monitor the gas analysis system through a network.

BRIEF DESCRIPTION OF THE DRAWINGS

The aforementioned objects, features and advantages of the invention will become apparent by referring to the following detailed description of the preferred embodiment with reference to the accompanying drawings, wherein.

DETAILED DESCRIPTION OF THE INVENTION

Figure 1:
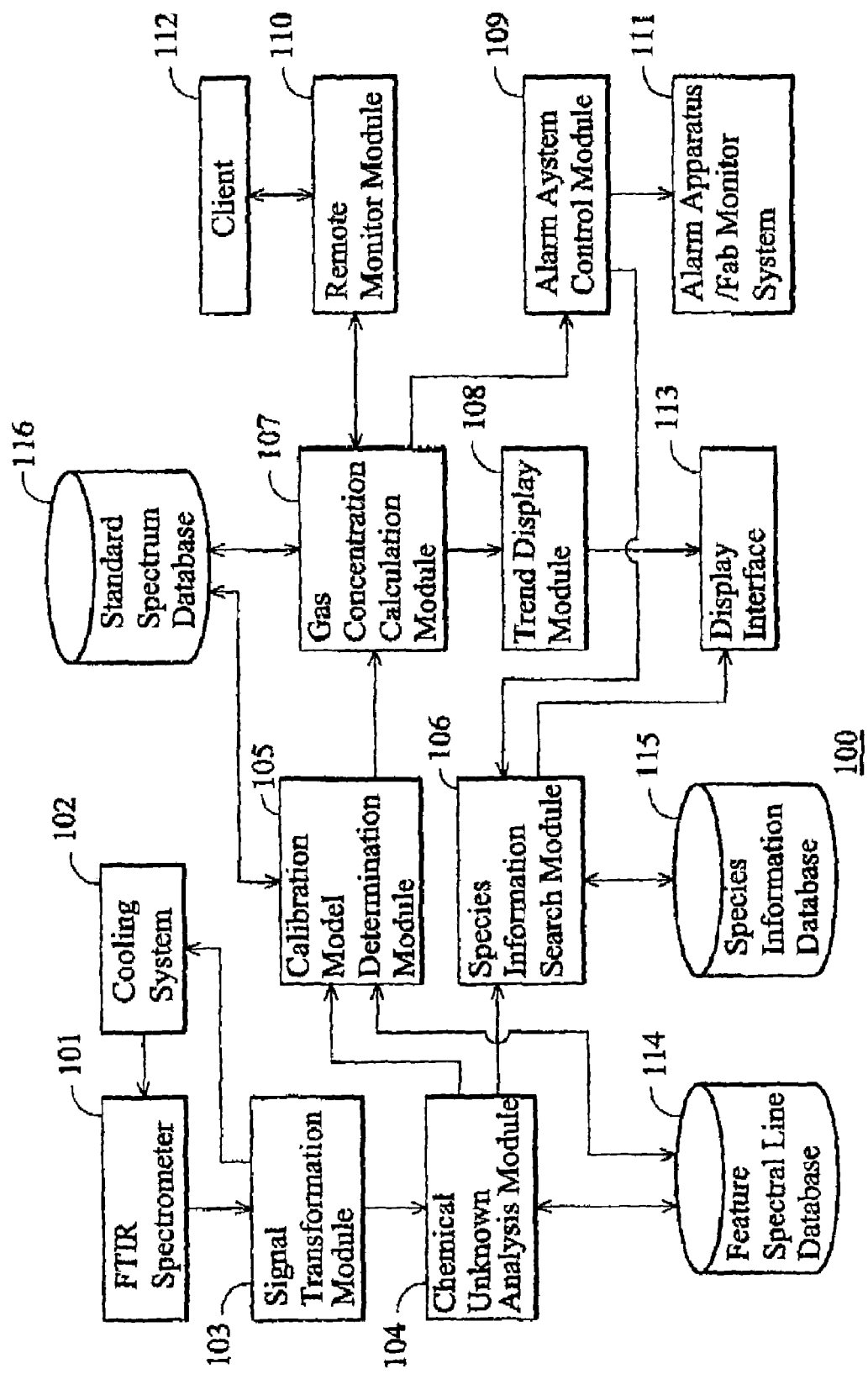
FIG. 1 is a schematic diagram illustrating the architecture of the gas analysis system according to the embodiment of the present invention.

FIG. 1 illustrates the architecture of the gas analysis system according to the embodiment of the present invention.

The gas analysis system 100 according to the embodiment of the present invention includes a Fourier transform infrared (FTIR) spectrometer 101, a cooling system 102, a signal transformation module 103, an unknown chemical analysis module 104, a calibration model determination module 105, a species information search module 106, a gas concentration calculation module 107, a trend display module 108, an alarm system control module 109, a remote monitor module. 110, an alarm apparatus/fab monitor system 111, a client 112, a display interface 113, a feature spectral line database 114, a species information database 115 and a standard spectrum database 116.

The FTIR spectrometer 101 includes an IR source, an interferometer, an optics system and a detector, and detects the interferogram of infrared radiation according to the interference theorem of light. The interferogram is a relational diagram of the intensity of IR source and time.

The FTIR spectrometer 101 may be an extractive FTIR spectrometer or an open-path FTIR spectrometer. The difference between the extractive and open-path FTIR spectrometers is that the extractive FTIR spectrometer has a gas cell to contain the gas. It should be noted that any kinds of the FTIR spectrometer can be applied to the present invention.

Since some detector of FTIR spectrometer 101 must work at a predetermined temperature, such as 77K (subzero 190 degrees centigrade) to obtain optimum results, the cooling system 102 can automatically replenish coolant in the FTIR spectrometer 101, so as to keep the FTIR spectrometer 101, and enable the FTIR spectrometer 101 for long-term detection.

The signal transformation module 103 receives electronic signals corresponding respectively to a reference (background) interferogram and a sample interferogram corresponding to a sample gas from the FTIR spectrometer 101 via a connection interface, such as a data acquisition adapter, RS232 serial port or network interface. The signal transformation module 103 then calculates an absorption spectrum of the sample gas according to the background interferogram and the sample interferogram. The background interferogram is the interferogram of the gas without the sample gas. It should be noted that the interferogram can be easily transformed into a frequency-based absorption spectrum using Fourier transformation, and the detailed operations are omitted here. Further, the transformation of the absorption spectrum is performed in the signal transformation module 103. However, some FTIR spectrometers 101 can perform the transformation of the absorption spectrum directly. In this case, the transformation of the signal transformation module 103 can be omitted.

Figure 2:
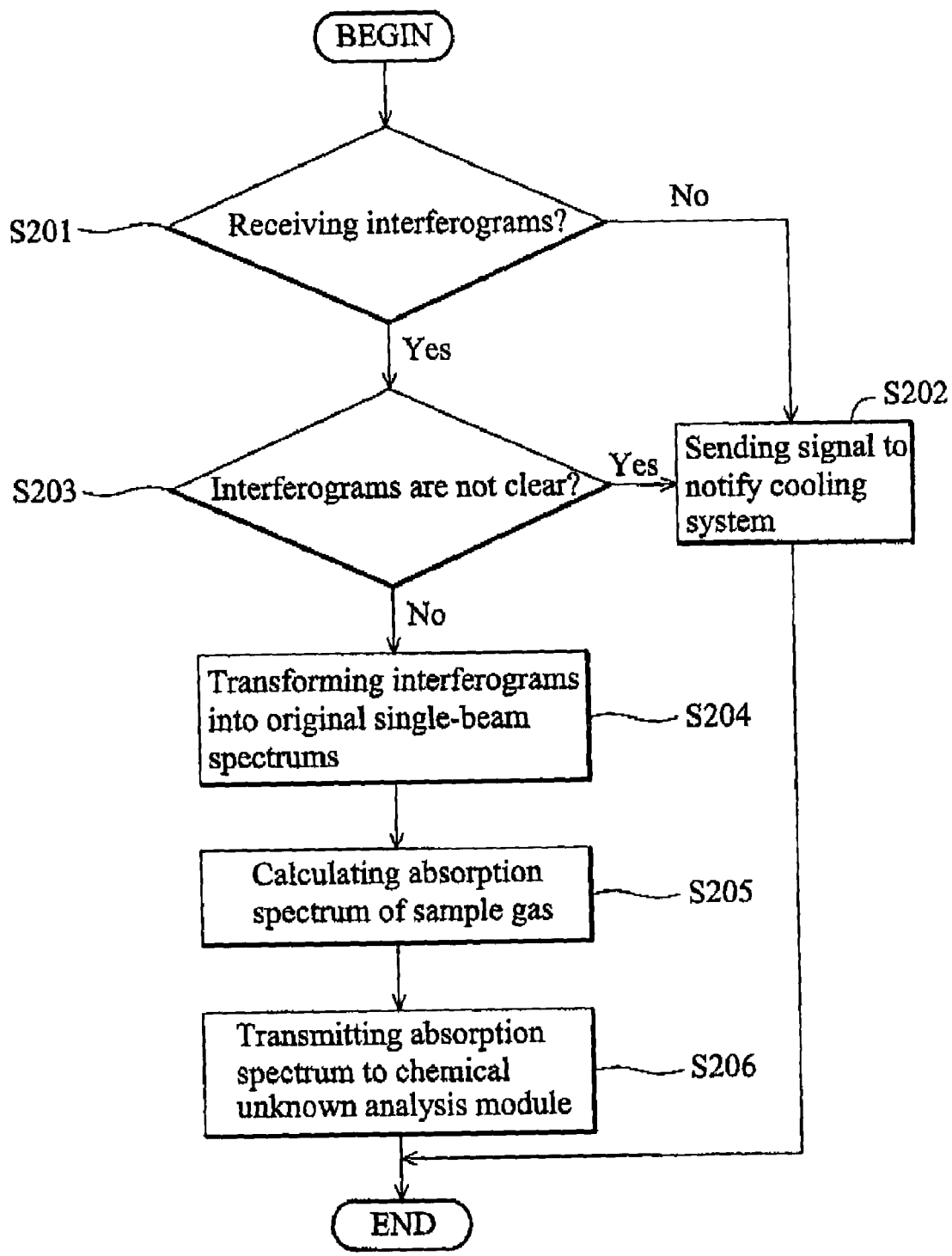
FIG. 2 is a flowchart showing the signal transformation process according to the embodiment of the present invention.

FIG. 2 shows the signal transformation process of the signal transformation module 103 according to the embodiment of the present invention. First, in step S201, the signal transformation module 103 checks whether interferograms have been received from the FTIR spectrometer 101. If the signal transformation module 103 cannot receive sample interferograms from the FTIR spectrometer 101 (No in step S201), in step 5202, the signal transformation module 103 sends a signal to notify the cooling system 102. After receiving the signal, the cooling system 102 may replenish coolant in the detector of FTIR spectrometer 101, so as to keep the detector of FTIR spectrometer 101 within the predetermined temperature range.

If yes (Yes in step S201), in step S203, the signal transformation module 103 checks whether the interferograms are clear enough by checking the intensity of the electronic signals corresponding to sample intererograms and the signal-to-noise ratio. If the interferograms are not clear (Yes in step S203), in step S202, the signal transformation module 103 sends a signal to notify the cooling system 102. Similarly, after receiving the signal, the cooling system 102 may replenish coolant in the detector of FTIR spectrometer 101, so as to keep the detector of FTIR spectrometer 101 within the predetermined temperature range.

If the interferograms are clear (No in step S203), in step S204, the signal transformation module 103 respectively transforms the background and sample time-based interferograms into corresponding original frequency-based single beam spectra using Fourier transformation. Then, in step S205, the absorption spectrum of the sample gas is calculated by the background spectrum and sample spectrum. Thereafter, in step S206, the signal transformation module 103 transmits the absorption spectrum to the unknown chemical analysis module 104.

Figure 3:
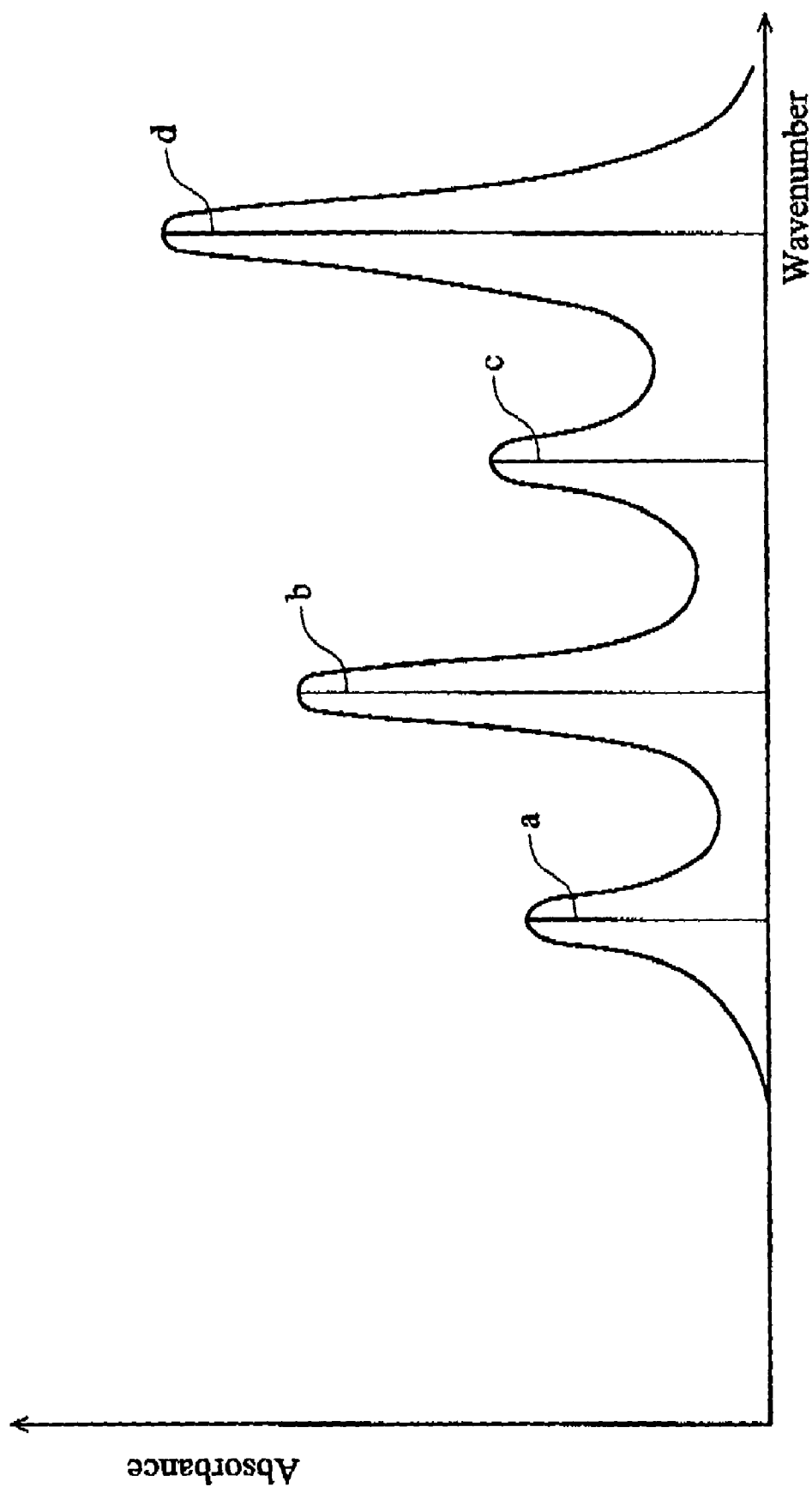
FIG. 3 is an example of an absorption spectrum.

The unknown chemical analysis module 104 qualitatively analyzes the absorption spectrum of the sample gas. The unknown chemical analysis module 104 compares each spectral line of the absorption spectrum with feature spectral lines recorded in the feature spectral line database 114 to determine the chemical species contained in the sample gas. FIG. 3 shows an example of the absorption spectrum. In this case, there are four main spectral lines in the absorption spectrum: a, b, c and d. It should be noted that the unknown chemical analysis module 104 can recognize all chemical species contained in the sample gas if the sample contains several substances.

After the chemical species contained in the sample gas are recognized, the species information search module 106 may retrieve related information for each chemical species from the species information database 115 according to each chemical species, and displays the retrieved related information of each chemical species in the display interface 113. The related information may include physical and chemical property, odor feature and potential hazard. In addition, the species information search module 106 may provide a user interface to receive queries, such as odor and corrosiveness from users, and search corresponding chemical species according to the queried information. Further, if the alarm system control module 109 sends the alarm signal, the species information search module 106 displays the retrieved information of the chemical species in the display interface 113. The operation of the alarm system control module 109 is discussed later.

In addition, after the unknown chemical analysis module 104 recognizes the chemical species contained in the sample gas, the calibration model determination module 105 can determine the calibration models used to calculate the gas concentration corresponding to the chemical species in the sample gas respectively. The calibration model determination module 105 has analysis conditions if the features spectral lines partially overlap. Further, the calibration model determination module 105 may retrieve a calculation region for each chemical species in the absorption spectrum from the feature spectral line database 114, and retrieve a standard spectrum of an expected concentration for each chemical species from the standard spectrum database 116. The calibration model includes the calculation regions for all chemical species in the absorption spectrum and/or overlapping conditions of these calculation regions.

For example, if there are three chemical species, A, B and C in the sample gas, the available calculation regions for A, B and C are Ra1; Rc1, Rb2, Rb3; and Rc1, Rc2 respectively, the maximum absorbance of each calculation regions for chemical species B and c are Rb3>Rb1>Rb2 and Rc2>Rc1 respectively, and Rb3, Rb1 and Rb2 overlap with the calculation regions for chemical species A and C, in which Rb2 and Rc1 has the minimum overlap.

First, the chemical species are sorted according to the number of available calculation regions, in which the order of A, C and B is obtained. Then, the calculation region for each chemical species is determined according to the order and the absorbance of its available calculation regions. In this case, first, the calculation region for chemical species A is selected as Ra1. Then, since the calculation regions for chemical species A and C have no overlap, the calculation region Rc2 with highest absorbance is selected as the calculation region for chemical species C. Afterward, since the calculation regions Rb3, Rb1 and Rb2 overlap with the calculation regions for chemical species A and C, and Rb2 and Rc1 has the minimum overlap, the calculation region Rb2 is selected as the calculation region for chemical species B. It should be noted that the overlap situation of the calculation regions Rb2 and Rc1 is also recorded. After the calculation regions for each chemical species are selected, the calibration model for the sample gas is determined.

The gas concentration calculation module 107 calculates the gas concentration of each chemical species according to the absorption spectrum, the calibration model and the standard spectra for each chemical species using the method of multivariate least squares and Bill's law. It should be noted that if there is no overlap between the calculation regions, the concentration for each chemical species can be calculated using the integral method to calculate the area of each calculation region, and performing geometric operations with the area and concentration of the corresponding standard spectrum. If the there are overlaps, the concentration for each chemical species can be calculated using the curve fitting method or the multivariate analysis method, so as to obtain precise results.

After the gas concentration of each chemical species is calculated, the gas concentration calculation module 107 sends the gas concentration to the trend display module 108. The trend display module 108 may display the gas concentration of each chemical species in the display interface 113 individually or collectively. With time, the trend display module 108 also displays the trend of the gas concentration of each chemical species in the display interface 113.

Further, the gas concentration calculation module 107 sends the gas concentration to the alarm system control module 109. The alarm system control module 109 may record preset value, such as TLV (threshold limit value) corresponding to each chemical species. The alarm system control module 109 sends an alarm signal it the gas concentration of any chemical species exceeds its respective preset value. As described above, the species information search module 106 displays the retrieved information of the chemical species in the display interface 113 if the species information search module 106 receives the alarm signal. Furthermore, the alarm apparatus/fab monitor system 111 set up in the factory may be coupled with the alarm system control module 109. If the alarm signal is received, the alarm apparatus/fab monitor system 111 may notify relevant personnel by alarm bell, message, email, beeper, or phone, and provide related information, such as the chemical species and its corresponding gas concentration, to emergency response crews.

The remote monitor module 110 provides the client 112 with authorization to monitor the gas concentration of each chemical species and the components of the gas analysis system 100 through a network, such as a wireless network or Internet.

Figure 4:
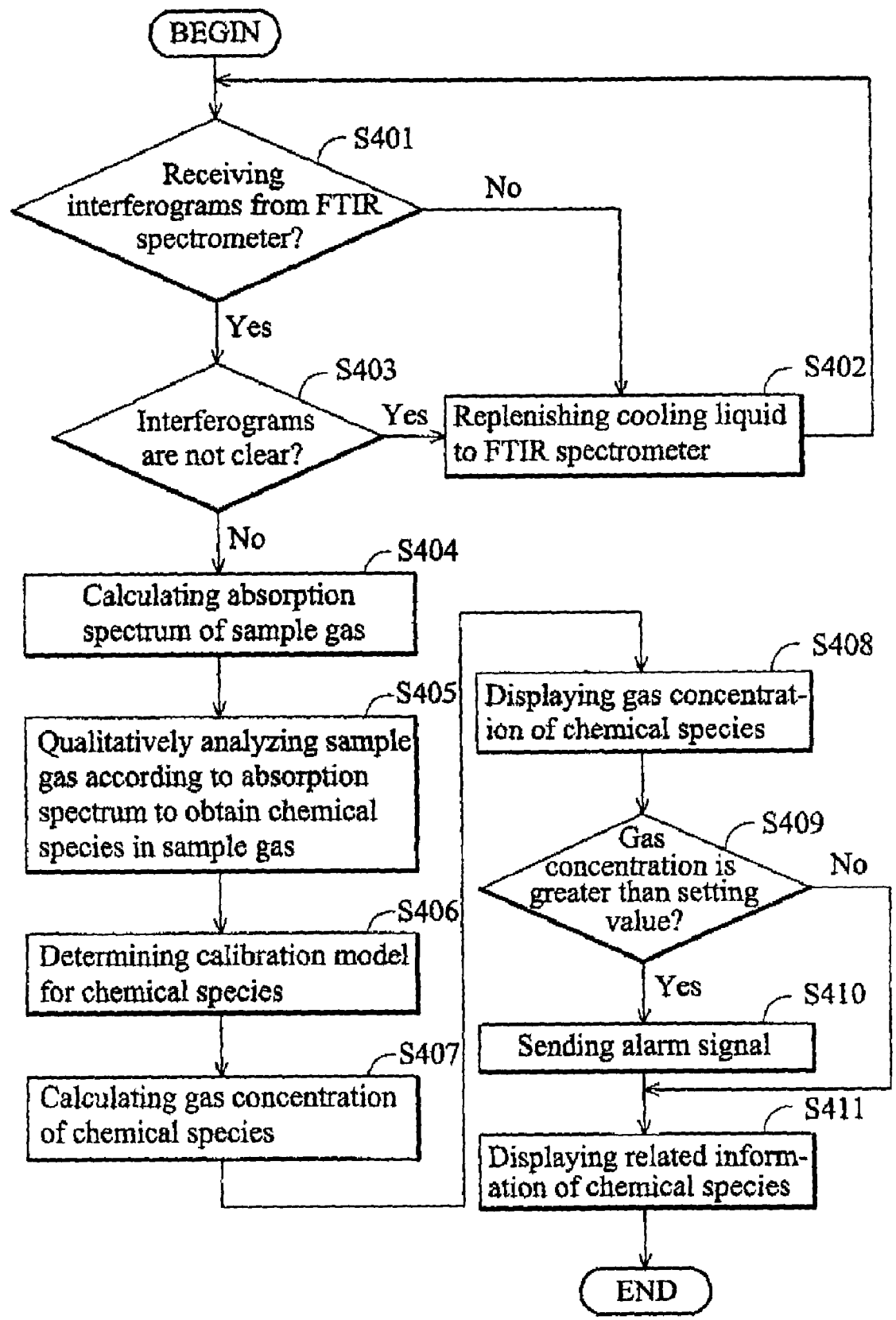
FIG. 4 is a flowchart showing the process of the gas analysis method according to the embodiment of the present invention.

FIG. 4 shows the process of the gas analysis method according to the embodiment of the present invention. First, in step S401, the signal transformation module 103 checks whether interferograms are received from the FTIR spectrometer 101. If the signal transformation module 103 cannot receive interferograms from the FTIR spectrometer 101 (No in step S401), in step S402, the signal transformation module 103 sends a signal to notify the cooling system 102, and the cooling system 102 replenishes coolant in the detector of FTIR spectrometer 101 according to the signal, so as to keep the detector of FTIR spectrometer 101 within the predetermined temperature range, and then the flow returns to step S401.

If yes (Yes in step S401), in step S403, the signal transformation module 103 checks whether the interferograms are clear enough by checking the intensity of the electronic signals corresponding to sample interferograms and the signal-to-noise ratio. If the interferograms are not clear (Yes in step S403), in step S402, the signal transformation module 103 sends a signal to notify the cooling system 102. Similarly, after receiving the signal, the cooling system 102 may replenish coolant in the detector of FTIR spectrometer 101, so as to keep the detector of FTIR spectrometer 101 within the predetermined temperature range, and then the flow returns to step S401.

If the interferograms are clear (No in step S403), in step S404, the absorption spectrum of the sample gas is calculated according to the background and sample interferograms. Thereafter, in step S405, the unknown chemical analysis module 104 qualitatively analyzes the absorption spectrum of the sample gas, and in step S406, the calibration model determination module 105 determines calibration models used to calculate the gas concentration corresponding to the chemical species in the sample gas respectively.

Afterward, in step S407, the gas concentration calculation module 107 calculates the gas concentration of each chemical species according to the absorption spectrum, the calibration model and the standard spectra for each chemical species using the method of least squares and Bill's law. Then, in step S408, the trend display module 108 displays the gas concentration of each chemical species in the display interface 113 individually or collectively, and the trend of the gas concentration of each chemical species of times in the display interface 113.

Then, in step S409, the alarm system control module 109 checks the gas concentration of each chemical species. If the gas concentration of any chemical species exceeds its respective preset value (Yes in step S409), in step S410, the alarm system control module 109 sends an alarm signal to notify relevant personnel. Then, in step S411, the species information search module 106 searches and displays the retrieved information of the chemical species in the display interface 113. Otherwise, if the gas concentration of each chemical species does not exceed its respective preset value (No in step S409), in step S411, the species information search module 106 displays the retrieved information of the chemical species in the display interface 113.

As a result, using the gas analysis system and method according to the present invention, the chemical species and gas concentration of the sample gas can be automatically analyzed using the absorption spectrum thereof. Further, the system can be remote monitored through a wireless network or Internet, and integrated with the alarm apparatus or fab monitor system to send a real-time alarm signal if the concentration of any chemical species exceeds its respective preset value.

Although the present invention has been described in its preferred embodiments, it is not intended to limit the invention to the precise embodiments disclosed herein. Those who are skilled in this technology can still make various alterations and modifications without departing from the scope and spirit of this invention. Therefore, the scope of the present invention shall be defined and protected by the following claims and their equivalents.

What is claimed is:

1. A gas analysis system, comprising: a FTIR (Fourier transform infrared) spectrometer; a signal transformation module operable to receive electronic signals corresponding respectively to a background interferogram and a sample interferogram corresponding to a sample gas from the FTIR spectrometer for further calculation to obtain an absorption spectrum of the sample gas according to the background interferogram and the sample interferogram; an unknown chemical analysis module operable to qualitatively analyze the sample gas according to the absorption spectrum alone to determine chemical species contained in the sample gas according to the absorption spectrum alone; a calibration model determination module operable to determine a calibration model according to the chemical species determined to be in the sample gas by the unknown chemical analysis module after the operation of the unknown chemical analysis module; and a gas concentration calculation module operable to calculate the gas concentration of the chemical species according to the absorption spectrum, the calibration model and a standard spectrum of the chemical species after the operations of the unknown chemical analysis module and the calibration model determination module.

2. The gas analysis system as claimed in claim 1 further comprising an alarm system control module to send an alarm signal if the gas concentration of the chemical species exceeds a respective preset value.

3. The gas analysis system as claimed in claim 2 further comprising a species information search module to retrieve related information according to the detected chemical species of the sample gas.

4. The gas analysis system as claimed in claim 3 wherein the species information search module further displays the related information of the chemical species in a display interface if the alarm system control module sends the alarm signal.

5. The gas analysis system as claimed in claim 3 wherein the related information comprises physical and chemical property, odor feature, and potential hazard information.

6. The gas analysis system as claimed in claim 1 further comprising a trend display module to display the trend of the gas concentration of the chemical species of the times in figures.

7. The gas analysis system as claimed in claim 1 further comprising a cooling system to automatically replenish coolant in a detector of the FTIR spectrometer.

8. The gas analysis system as claimed in claim 7 wherein the cooling system further replenishes coolant in the detector of the FTIR spectrometer if the signal transformation module cannot receive the electronic signals from the FTIR spectrometer.

9. The gas analysis system as claimed in claim 1 further comprising a remote monitor module to receive instructions to monitor the gas analysis system through a network.

10. The gas analysis system as claimed in claim 1 wherein the FTIR spectrometer is an extractive FTIR spectrometer.

11. The gas analysis system as claimed in claim 1 wherein the FTIR spectrometer is an open-path FTIR spectrometer.

12. The gas analysis system as claimed in claim 1 further comprising a feature spectral line database to store feature spectral lines corresponding to the chemical species.

13. The gas analysis system as claimed in claim 12 wherein the unknown chemical analysis module compares spectral lines of the absorption spectrum with the feature spectral lines recorded in the feature spectral line database to determine the chemical species in the sample gas.

14. The gas analysis system as claimed in claim 12, wherein the calibration model determination module retrieves a calculation region for each chemical species determined to be in the sample gas from the feature spectral line database.

15. The gas analysis system as claimed in claim 14, further including a standard spectrum database, wherein the calibration model determination module retrieves a standard spectrum for each chemical species determined to be in the sample gas.

16. The gas analysis system as claimed in claim 15, wherein the calibration model determination module determines the calibration model according to whether the feature spectral lines of the chemical species determined to be in the sample gas partially overlap, and the determined calibration module includes the calculation regions for all the chemical species in the absorption spectrum and overlapping conditions of the calculation regions.

17. The gas analysis system as claimed in claim 1 wherein the gas concentration calculation module calculates the gas concentration of the chemical species according to the absorption spectrum, the calibration model and the standard spectra of the chemical species using multivariate least squares and Bill's law methodology.

18. The gas analysis system as claimed in claim 1 wherein the calibration model comprises an analytical region corresponding to each chemical in the sample gas.

* * * * *